(12) United States Patent
Elokdah et al.

(10) Patent No.: US 6,472,430 B2
(45) Date of Patent: Oct. 29, 2002

(54) AMINO THIOXOMETHYL AMINO OXYACETIC ACID DERIVATIVES

(76) Inventors: Hassan M. Elokdah, 1487 Merrick Rd., Yardley, PA (US) 19067; Theodore S. Sulkowski, 316 Rockland Rd., Wayne, PA (US) 19087

( * ) Notice: Subject to any disclaimer, the term of this patent is extended or adjusted under 35 U.S.C. 154(b) by 0 days.

(21) Appl. No.: 09/965,898

(22) Filed: Sep. 28, 2001

(65) Prior Publication Data

US 2002/0045776 A1 Apr. 18, 2002

Related U.S. Application Data

(60) Provisional application No. 60/237,466, filed on Oct. 2, 2000.

(51) Int. Cl.⁷ .......................... A01N 37/18; C07C 32/00; C07C 335/00
(52) U.S. Cl. .......................... 514/542; 514/562; 560/16; 562/428; 564/17
(58) Field of Search ................. 560/16; 562/428; 564/17; 514/542, 562

(56) References Cited

U.S. PATENT DOCUMENTS

| 3,282,987 A | 11/1966 | Ellis |
| 3,438,985 A | 4/1969 | Bernstein |
| 3,625,968 A | 12/1971 | Zschocke |

FOREIGN PATENT DOCUMENTS

| EP | 0 528 146 A1 | 2/1993 |
| FR | 1432738 | 3/1966 |

OTHER PUBLICATIONS

Frank, A et al Monatsh Chem. 92 (1961) p. 725–739 see (Beilstein Reg No. (BRN) 2756589).*
Gofman et al, Circulation, 34, 1966, 679–697.
Miller and Miller, Lancet, 1, 1975, 16–19.
Gordon et al, Circulation, 79, 1989, 8–15.
Stampfer et al, N. Engl. J. Med., 325, 1991, 373–381.
Badimon et al, Lab. Invest., 60, 1989, 455–461.
Miller et al, Br. Med. J., 282, 1981, 1741–1744.
Picardo et al, Arteriosclerosis, 6, 1986, 434–441.
Glomset, J. Lipid Res., 9, 1968, 155–167.
Glass et al, J. Biol. Chem., 258, 1983, 7161–7167.
MacKinnon et al., J. Biol. Chem., 261, 1986, 2548–2552.
Grow and Fried, J. Biol. Chem., 253, 1978, 1834–1841.
Lagocki and Scanu, J. Biol. Chem., 255, 1980, 3701–3706.
Schaefer et al, J. Lipid Res., 23 1982, 1259–1273.

* cited by examiner

Primary Examiner—Paul J. Killos
(74) Attorney, Agent, or Firm—Michael R. Nagy

(57) ABSTRACT

Antiatherosclerotic compounds are provided which have the following structure:

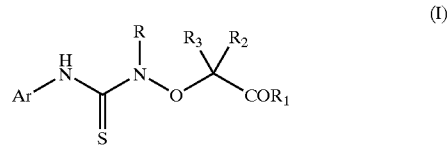

wherein

R is lower alkyl;

$R_1$ is hydroxy, amino, or lower alkoxy, $R_2$ and $R_3$ are each independently hydrogen, alkyl or aryl;

Ar is phenyl, indanyl, benzhydryl, or phenyl substituted with one or more member selected from the group consisting of halogen, lower alkyl, perfluoroalkyl, lower alkoxy, perfluoroalkylalkoxy, dialkylamino, and aryloxy; or pharmaceutically acceptable salts thereof.

14 Claims, No Drawings

AMINO THIOXOMETHYL AMINO OXYACETIC ACID DERIVATIVES

This application claims priority from copending provisional application Serial Number 60/237,466, filed Oct. 2, 2000, the entire disclosure of which is hereby incorporated by reference.

FIELD OF THE INVENTION

The invention is directed to anti-atherosclerotic agents and more specifically, to compounds, compositions and methods for treating atherosclerotic conditions, such as dyslipoproteinemias and coronary heart disease. This invention specifically relates to amino thioxomethyl amino oxyacetic acid derivatives that elevate HDL cholesterol concentration and which may be useful for the treatment of atherosclerotic conditions such as, coronary heart disease.

BACKGROUND OF THE INVENTION

Numerous studies have demonstrated that both the risk of coronary heart disease (CHD) in humans and the severity of experimental atherosclerosis in animals are inversely correlated with serum HDL cholesterol (HDL-C) concentrations (Ross et al, *Am. J. Med.*, 11 (1951) 480–493; Gofman et al, *Circulation*, 34 (1966) 679–697; Miller and Miller, *Lancet* 1 (1975) 16–19; Gordon et al, *Circulation* 79 (1989) 8–15; Stampfer et al, *N. Engl. J. Med.*, 325 (1991) 373–381; Badimon et al, *Lab. Invest.*, 60 (1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated level of some HDL particles in humans appears to be correlated to a decreased number of sites of stenosis in the coronary arteries of humans (Miller et al, *Br. Med. J.*, 282 (1981) 1741–1744).

There are several mechanisms by which HDL may protect against the progression of atherosclerosis. Studies in vitro have shown that HDL is capable of removing cholesterol from cells (Picardo et al, *Arteriosclerosis*, 6 (1986) 434–441). Data of this nature suggest that one antiatherogenic property of HDL may lie in its ability to deplete tissues of excess free cholesterol and eventually lead to the delivery of this cholesterol to the liver (Glomset, *J. Lipid Res.*, 9 (1968) 155–167). This has been supported by experiments showing efficient transfer of cholesterol from HDL to the liver (Glass et al, *J. Biol. Chem.*, 258 (1983) 7161–7167; MacKinnon et al, *J. Biol. Chem.*, 261 (1986) 2548–2552). In addition, HDL may serve as a reservoir in the circulation for apoproteins necessary for the rapid metabolism of triglyceride-rich lipoproteins (Grow and Fried, *J. Biol. Chem.*, 253 (1978) 1834–1841; Lagocki and Scanu, *J. Biol. Chem.*, 255 (1980) 3701–3706; Schaefer et al, *J. Lipid Res.*, 23 (1982) 1259–1273). Accordingly, agents which increase HDL cholesterol concentrations are useful as anti-atherosclerotic agents, particularly in the treatment of dyslipoproteinemias and coronary heart disease.

Ureas, thioureas and derivatives thereof are known to be useful for treating various conditions. For example, European Patent No. 528 148 A1 discloses the use of N-phenyl thiourea derivatives (1) for the treatment of atherosclerosis by elevation of HDL-C serum levels. Among the compounds disclosed is 5-chloro-2-methylphenyl thioureido acetic acid (2). In all cases, one of $R_1$ or $R_2$ is hydrogen.

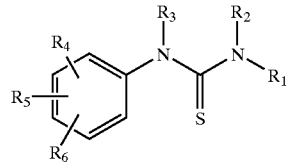

(1)

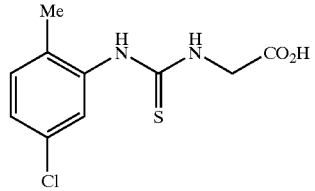

(2)

U.S. Pat. No. 3,282,987 claims the use of α-ureidooxy carboxylic acids (3) and their derivatives as plant growth regulators and herbicides.

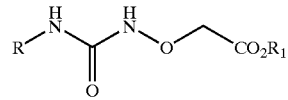

(3)

where R is hydrogen, alkyl, or chlorophenyl; and $R_1$ is hydrogen, or alkyl of 1–12 carbons.

U.S. Pat. No. 3,625,968 discloses compounds of the formula, $R_1$ and R2 may be identical or different and each denotes aliphatic, araliphatic, cycloaliphatic, or aromatic; $R_1$ may also be hydrogen.

U.S. Pat. No. 3,438,985 discloses similar compounds where $R_1$ and $R_2$ represents hydrogen or lower alkyl.

French Patent No. 1,432,738 also discloses similar compounds where $R_1$ is lower alkyl and $R_2$ is hydrogen.

SUMMARY OF THE INVENTION

In accordance with this invention there is provided thioxomethyl aminoxy acetic acid derivatives of Formula I:

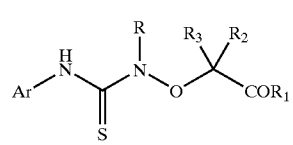

(I)

wherein

R is lower alkyl;

$R_1$ is hydroxy, amino, or lower alkoxy;

$R_2$ and $R_3$ are each independently hydrogen, alkyl or aryl;

Ar is phenyl, indanyl, benzhydryl, or phenyl substituted with one or more members of the group consisting of halogen, lower alkyl, perfluoroalkyl, lower alkoxy, perfluoroalkylalkoxy, dialkylamino, and aryloxy; or pharmaceutically acceptable salts thereof.

This invention also provides methods of elevating HDL concentration and treating or inhibiting atherosclerosis and related coronary heart disease or dyslipoproteinemias and increasing the HDL cholesterol concentration in a mammal in need thereof comprising administering to and said mammal an effective amount of a compound of Formula I:

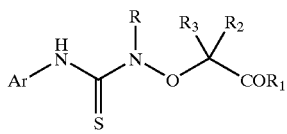

wherein
R is lower alkyl;
R₁ is hydroxy, amino, or lower alkoxy,
R₂ and R₃ are each independently hydrogen, alkyl or aryl;
Ar is phenyl, indanyl, benzhydryl, or phenyl substituted with one or more members of the group consisting of halogen, lower alkyl, perfluoroalkyl, lower alkoxy, perfluoroalkylalkoxy, dialkylamino, and aryloxy; or pharmaceutically acceptable salts thereof.

DETAILED DESCRIPTION OF THE INVENTION

Preferably, the present compounds are those represented by Formula I:

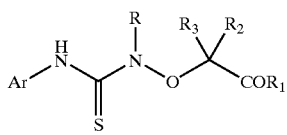

wherein
R is lower alkyl;
R₁ is lower alkoxy;
R₂ and R₃ are hydrogen;
Ar is phenyl, indanyl, or phenyl substituted with one or more members selected from the group consisting of halogen, lower alkyl, lower alkoxy, and aryloxy; or pharmaceutically acceptable salts thereof.

As used in the present application, the term "lower alkyl" and "lower alkoxy" include both straight chain and branched moieties having 1–6 carbon atoms. The term "alkyl" also included branched and straight chain moieties and is not limited in carbon number. The term "aryl" includes aromatic radicals of 6–12 carbon atoms. The term "halogen" includes fluorine, chlorine, bromine and iodine.

The pharmaceutically acceptable salts of the present compounds include those derived from organic and inorganic acids such as, but not limited to: acetic, lactic, citric, tartaric, succinic, fumaric, maleic, malonic, mandelic, malic, hydrochloric, hydrotoronic, phosphoric, nitric, sulfuric, methanesulfonic, toluene sulfonic, and similarly known, acceptable acids. The most preferred compounds of this invention are:

Ethyl [[[[(5-Chloro-2-methylphenyl)amino]thioxomethyl] methylamino]oxy]acetate;
Ethyl [[[[(4-Chloro-2-methylphenyl)amino]thioxomethyl] methylamino]oxy]acetate;
Ethyl [[[[(2,3-dihydro-1H-inden-5-yl)amino]thioxomethyl] methylamino]oxy]acetate;
Ethyl [[methyl[[(2-(1-methylethyl)phenyl]amino] thioxomethyl]methylamino]oxy]acetate;
Ethyl [[[[(2,5-dimethylphenyl)amino]thioxomethyl] methylamino]oxy]acetate;
Ethyl [[[[(2-methylpropyl)amino]thioxomethyl] methylamino]oxy]acetate;
Ethyl [[[[(4-phenoxyphenyl)amino]thioxomethyl] methylamino]oxy]acetate;
Ethyl [[[[(4-Chloro-2-methylphenyl)amino]thioxomethyl] ethylamino]oxy]acetate.;
Ethyl [[[[(5-Chloro-2-methylphenyl)amino]thioxomethyl] (1-methylethyl)amino]oxy]acetate; and
Ethyl [[[[(5-Chloro-2-methylphenyl)amino]thioxomethyl] (1-methylpropyl)amino]oxy]acetate The compounds of the invention may be prepared readily according to the following reaction scheme or modification thereof using readily available starting materials, reagents and conventional synthetic procedures. It is also possible to make use of variants of these process steps, which in themselves are known to and well within the preparatory skill of the medicinal chemist.

In reaction scheme IR is alkyl, R₁ is alkyl, alkenyl, alkynyl, benzyl, aryl or substituted aryl, R₂ and R₃ are independently hydrogen, alkyl, alkenyl, alkynyl, benzyl, aryl or substituted aryl, Ar is phenyl, indanyl, benzhydryl, or phenyl optionally substituted with one or more groups selected from halogen, lower alkyl, perfluoroalkyl, lower alkoxy, perfluoroalkylalkoxy, dialkylamino, or aryloxy.

SCHEME I

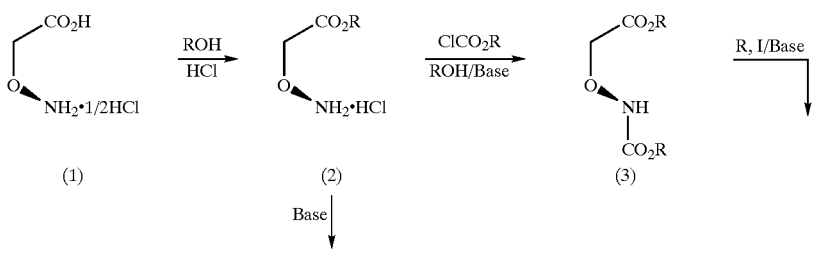

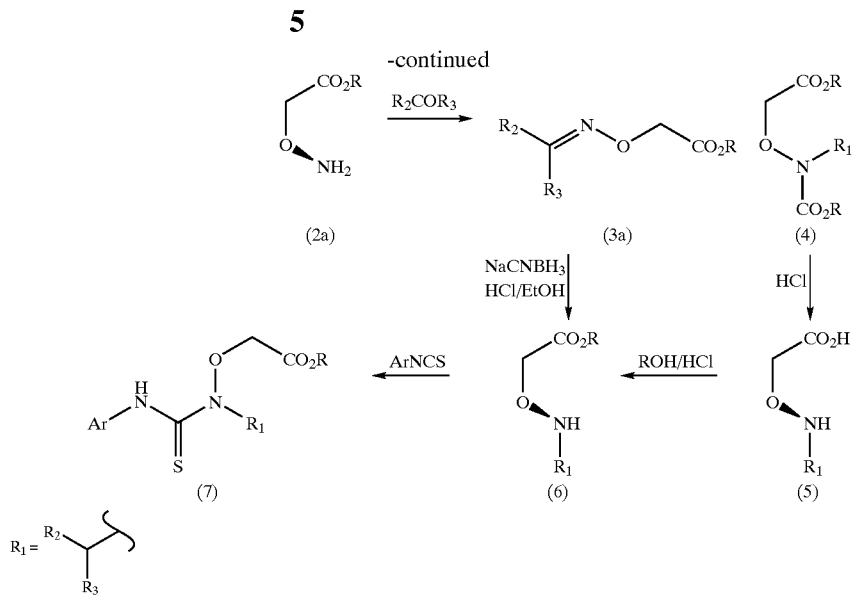

Carboxymethoxylamine hemihydrochloride (1) was esterified with the appropriate alcohol saturated with hydrogen chloride. The reaction was carried out at ambient temperature for 24 hours. The hydrochloride salt of the ester (2) was obtained. Reaction of 2 with ethyl- or methylchloroformate in alcohol in the presence of base such as sodium bicarbonate afforded the oxy-carbamate (3). This reaction was carried out at ambient temperature over a period of 3–5 hours. Compound (3) was alkylated with alkyl iodides (excess) by refluxing in alcohol under basic conditions over a period of 2 to 3 hours affording 4. Hydrolysis of 4 to the N-alkyl-carboxymethoxylamine hydrochloride (5) was carried out by refluxing with hydrochloric acid over 20 minutes to one hour period. Esterification of 5 with the appropriate alcohol saturated with hydrogen chloride followed by basic workup afforded the N-alkyl-aminoxyacetate (6). Alternatively, ethyl aminoxy acetate (2a) was liberated from its hydrochloride salt with base, reaction of 2 with 2–5 fold excess of aldehydes or ketones either neat or in alcohol over a period of 1 to 4 hours under reflux afforded the imine (3a). Hydride reduction of (3a) under acidic condition in a solvent such as an alcohol followed by basic workup afforded the amine (6). Reaction of (6) with isothiocyanates in a solvent such as chloroform or ether over a period of 20 minutes to 1 hour provided compound (7).

The ability of the compounds of this invention to increase blood serum HDL levels was evaluated by the following standard experimental procedure for determination of HDL cholesterol:

Male Sprague-Dawley rats weighing 200–225 g were housed two per cage and fed Purina Rodent Chow Special Mix 5001-S supplemented with 0.25% cholic acid and 1.0% cholesterol and water ad libitum for 8 days. Each test substance was administered to a group of six rats fed the same diet with the test diet mixed in as 0.005–0.1% of the total diet. Body weight and food consumption were recorded prior to diet administration and at termination. Typical doses of the test substances are 5–100 mg/kg/day.

At termination, blood was collected from anesthetized rats and the serum was separated by centrifugation. Total serum cholesterol was assayed using the Sigma Diagnostics enzymatic kit for the determination of cholesterol, Procedure No. 352, modified for use with ninety-six well microtiter plates. After reconstitution with water the reagent contained 300 U/l cholesterol oxidase, 100 U/l cholesterol esterase, 1000 U/l horseradish peroxidase, 0.3 moles/l 4-aminoantipyrine and 30.0 moles/l p-hydroxybenzenesulfonate in a pH 6.5 buffer. In the reaction cholesterol is oxidized to produce hydrogen peroxide which is used to form a quinoneimine dye. The concentration of dye formed is measured spectrophotometrically by absorbence at 490 nm after incubation at 25° C. for 30 minutes. The concentration of cholesterol was determined for each serum sample relative to a commercial standard from Sigma.

HDL cholesterol concentrations in serum were determined by separation of lipoprotein classes by fast protein liquid chromatography (FPLC) by a modification of the method of Kieft et al., *J. Lipid Res.*, 32 (1991) 859–866. 25 ul of serum was injected onto Superose 12 and Superose 6 (Pharmacia), in series, with a column buffer of 0.05 M Tris (2-amino-2-hydroxymethyl-1,3-propanediol) and 0.15 M sodium chloride at a flow rate of 0.5 ml/min. The eluted sample was mixed on line with Boehringer-Mannheim cholesterol reagent pumped at 0.2 ml/min. The combined eluents were mixed and incubated on line through a knitted coil (Applied Biosciences) maintained at a temperature of 45° C. The eluent was monitored by measuring absorbance at 490 nm and gave a continuous absorbance signal proportional to the cholesterol concentration. The relative concentration of each lipoprotein class was calculated as the per cent of total absorbency. HDL cholesterol concentration, in serum, was calculated as the per cent of total cholesterol as determined by FPLC multiplied by the total serum cholesterol concentration.

Test compounds were administered at a dose of 100 mg/kg. Each test substance was administered to a group of six rats. The duration of treatment was eight days. The compounds of the present invention were found to increase HDL cholesterol concentrations as summarized in Table I:

TABLE I

| Compound of Example | HDL Cholesterol Level Increase (%) |
|---|---|
| 1. | 118 |
| 2. | 62 |
| 3. | 146 |
| 4. | 104 |
| 5. | 40 |
| 6. | 17 |
| 7. | 35 |
| 8. | 90 |
| 9. | 46 |
| 10. | 39 |

This invention also provides pharmaceutical compositions comprised amino thioxo methyl aminoxy acetic acid derivatives either alone or in combination with excipients (i.e. pharmaceutically acceptable materials with no pharmacological effects). Such compositions are useful in the treatment of atherosclerotic conditions such as dyslipoproteinemias and coronary heart disease, in that they increase the blood serum high density lipoprotein concentration of mammals treated with the compounds.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid which is in admixture with the finely divided active ingredient. In tablets the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in suitable oil, such as arachis oil. Liquid pharmaceutical compositions which are sterile solutions or suspensions can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patient's recovery rate. By initiating the treatment regimen with a minimal daily dose of about one gram, the blood levels of HDL and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The following non-limiting examples illustrate the production of representative compounds of this invention.

N-Substituted Ethyl Aminooxy Acetate (6)
Procedure A
Step 1
Ethyl Aminooxy Acetate Hydrochloride Salt (2, R=Et)

Aminoxyacetic acid hemihydrochloride (500 g) was suspended in ethanol (2000 mL). The mixture was saturated with hydrogen chloride and allowed to stand at room temperature for 24 hours. The mixture was then concentrated to the precipitation point. The solid was collected by filtration, washed with ether and dried to give the title compound as a white solid (547 g), m.p. 115–117° C. Mass spectrum (EI, M.$^+$) m/z 119. $^1$H-NMR (DMSO-$d_6$; 300 MHz): δ11.08 (br s, 3H), 4.74 (s, 2H), 4.16 (q, 2H), and 1.21 ppm (t, 3H).

Anal.. for $C_4H_9NO_3$. HCl:
Calcd: C, 30.88; H, 6.48; N, 9.00.
Found: C, 30.55; H, 6.41; N, 9.16.
Step 2
Ethyl N-ethoxy Carbonyl Aminooxy Acetate (3, R=Et)

The mixture of ethyl aminooxy acetate hydrochloride (540 g), sodium bicarbonate (300 g), and ethanol (1700 mL) was vigorously stirred with a mechanical stirrer. Ethyl chloroformate (395 g) was added dropwise. Additional amount of sodium bicarbonate (300 g) was added in portions to keep the reaction mixture basic. The reaction mixture was stirred at ambient temperature for 3 hours. The mixture was then filtered. The solid was rinsed with fresh ethanol. The combined filtrate was evaporated to dryness. The residue was dissolved in ethyl acetate (1500 mL) and washed with water (2×500 mL). The organic phase was dried over anhydrous magnesium sulfate, filtered, and evaporated to an oily residue. The oily residue solidified into a crystalline mass upon standing. The solid mass was crushed and stirred in ether (200 mL). Collection of the solid by filtration and drying afforded the title compound (645 g), m.p. 37–39° C. Mass spectrum (+FAB, [M+H]$^+$) m/z 192. $^1$H-NMR (DMSO-d$_6$; 400 MHz): δ10.45 (s, 1H), 4.36 (s, 2H), 4.12 (q, 2H), 4.05 (q,2H), 1.19 (t, 3H), and 1.18 ppm (t, 3H).

Anal. for. C$_7$H$_{13}$NO$_5$:
Calcd.: C, 43.98; H, 6.85; N, 7.33.
Found: C, 43.99; H, 6.75; N, 7.52.

Step 3
Ethyl N-methyl N-ethoxy Carbonyl Aminooxy Acetate (4, R=Et, R$_1$=Me)

The mixture of ethyl N-ethoxy carbonyl aminooxy acetate (306 g), methyl iodide (455 g), potassium carbonate (400 g) and ethanol (500 mL) was heated at reflux for 3 hours, stirred at ambient temperature for 1 hours then filtered. The filtrate was evaporated to dryness. The residue was dissolved in ethyl acetate (1200 mL) and washed with water (3×700 mL). The organic phase was dried over anhydrous magnesium sulfate and evaporated to give (290.5 g) of ethyl N-methyl N-ethoxy carbonyl aminooxy acetate (4) as an oil. Mass spectrum (El, M.$^+$) m/z 205. $^1$H-NMR (DMSO-d$_6$; 400 MHz): δ4.49 (s, 2H), 4.14 (q, 2H), 4.10 (q, 2H), 3.13 (s, 3H), and 1.20 ppm (dt, 6H).

Step 4
N-methyl Aminooxy Acetic Acid Hydrochloride (5, R$_1$=Me)

A mixture of ethyl N-methyl N-ethoxy carbonyl aminooxy acetate (280 g ), hydrochloric acid (350 mL), and water (150 mL) was heated at reflux for 45 minutes then evaporated to dryness under vacuum. This afforded the title compound (170 g) as a semi solid. Mass spectrum (El, M.$^+$) m/z 105. $^1$H-NMR (DMSO-d$_6$; 400 MHz): δ13–11 (br.s, 1H), 4.71 (s, 2H), and 2.8 ppm (s, 3H)

Anal. for. C$_3$H$_7$NO$_3$.HCl:
Calcd.: C, 25.45; H, 5.70; N, 9.89.
Found: C, 25.52; H, 5.93; N, 10.08.

Step 5
Ethyl N-methyl Aminooxy Acetate (6, R=Et, R$_1$=Me)

A solution of N-methyl aminooxy acetic acid hydrochloride (9.5 g) in ethanol (100 mL) was saturated with hydrogen chloride. The mixture was allowed to stand at ambient temperature for 18 hours then evaporated to dryness. The residue was dissolved in water (100 mL)/ethyl acetate (300 mL). The mixture was saturated with solid sodium bicarbonate. The organic phase was washed with brine (100 mL), dried over anhydrous magnesium sulfate and evaporated to dryness. The title compound (7.8 g) was obtained as an oil. Mass spectrum (El, M.$^+$) m/z 133. $^1$H-NMR (DMSO-d$_6$; 300 MHz): δ6.84 (s, 1H), 4.15 (s, 2H), 4.10 (q, 2H), 2.53 (s, 3H), and 1.2 ppm (t, 3H).

Following the steps described in procedure A and substituting ethyl iodide for methyl iodide the following compound was prepared:

Ethyl N-ethyl Aminooxy Acetate (6, R=Et, R$_1$=Et)
$^1$H-NMR (DMSO-d$_6$; 300 MHz): δ6.75 (t, 1H), 4.18 (s, 2H), 4.12 (q, 2H), 2.82 (m, 2H), 1.2 (t, 3H), and 0.97 ppm (t, 3H).

Procedure B
Step 1
Ethyl Aminooxy Acetate (2,a R=Et)

Ethyl aminooxy acetate hydrochloride (2, R=Et) was prepared as described in step 1 of procedure A. Ethyl aminooxy acetate hydrochloride (24 g) was dissolved in water (100 mL). The solution was saturated with sodium bicarbonate and extracted with ethyl acetate (2×200 mL). The organic extract was washed with brine (200 mL), and dried over anhydrous magnesium sulfate. Evaporation of the solvent afforded the title compound (15.8 g) as an oil. $^1$H-NMR (DMSO-d$_6$; 300 MHz): δ6.28 (s, 2H), 4.12 (s, 2H), 4.10 (q, 2H), and 1.20 ppm (t, 3H).

Step 2
Ethyl Methyleneiminoxy Acetate (3a, R=Et, R$_2$=R$_3$=H)

The mixture of ethyl Aminooxy acetate (11.9 g), paraformaldehyde (3.0 g) and ethanol (100 mL) was heated at reflux for three hours. The reaction mixture was cooled to ambient temperature then filtered to remove the undissolved solid. Evaporation of the solvent afforded 12 g of the title compound as an oil; $^1$H-NMR (DMSO-d$_6$; 400 MHz): δ7.16 (d, 1H), 6.69 (d, 1H), 4.63 (s, 2H), 4.13 (q, 2H), and 1.20 ppm (t,3H).

Step 3
Ethyl N-methyl Aminooxy Acetate (6, R=Et, R$_1$=Me)

To a stirring solution of ethyl methyleneiminoxy acetate (11.8 g) in ethanol (75 mL) was added sodium cyanoborohydride (11.3 g). Ethanolic hydrogen chloride was then added to bring the pH to 1–2. The reaction mixture was stirred for 3 hours then evaporated to dryness. The residue was dissolved in ether (400 mL) and water (300 mL). The mixture was saturated with solid sodium bicarbonate. The organic phase was washed with brine (200 mL), and dried over anhydrous magnesium sulfate. Evaporation of the solvent afforded 7.0 g of the title compound as an oil. Mass spectrum (El, M.$^+$) m/z 133. $^1$H-NMR (DMSO-d$_6$; 300 MHz): δ6.84 (s,1H), 4.15 (s, 2H), 4.10 (q, 2H), 2.53 (s, 3H), and 1.2 ppm (t, 3H).

Following steps 1 to 3 as described in procedure B and using the appropriate aldehydes or ketones the following compounds were prepared:

Ethyl N-ethyl Aminooxy Acetate (6, R=Et, R$_1$=Et)
$^1$H-NMR (DMSO-d$_6$; 300 MHz): δ6.75 (t, 1H), 4.18 (s, 2H), 4.12 (q, 2H), 2.82 (m, 2H), 1.2 (t, 3H), and 0.97 ppm (t, 3H).

Ethyl N-isopropyl Aminooxy Acetate (6, R=Et, R$_1$=iso-Pr)
Mass spectrum (Cl, [M+H]$^+$) m/z 162. $^1$H-NMR (DMSO-d$_6$; 400 MHz): δ6.52 (d, 1H), 4.17 (s, 2H), 4.10 (q, 2H), 3.04 (m, 1H), 1.2 (t, 3H), and 0.93 ppm (d, 6H).

Ethyl N-isobutyl Aminooxy Acetate (6, R=Et, R$_1$=iso-Bu)
$^1$H-NMR (DMSO-d$_6$; 200 MHz): δ6.52 (d, 1H), 4.18 (s, 2H), 4.12 (q, 2H), 2.85 (m, 1H), 1.48 (m, 1H), 1.2 (m, 3H), 0.92 (d, 3H), and 0.83 ppm (t, 3H).

EXAMPLE 1

Ethyl [[[[(5-Chloro-2-methylphenyl)amino]thioxomethyl]methylamino]oxy]acetate

A mixture of 5-chloro-2-methylphenyl-isothiocyanate (11.0 g), ethyl N-methyl aminooxy acetate (7.98 g), and ether (50 mL) was stirred at ambient temperature for thirty minutes. The solvent was evaporated. Fresh ether (100 mL) was added. The mixture was evaporated to dryness. The solid mass was slurried in hexane. The solid was collected by filtration and dried to give the title compound (18.2 g) as a white solid, m.p. 83–84° C. Mass spectrum (+FAB, [M+H]$^+$) m/z 317/319. $^1$H-NMR (DMSO-d$_6$; 400 MHz) δ10.00 (s, 1H), 7.30–7.23 (m, 3H),4.71 (s, 2H), 4.18 (q, 2H), 3.55 (s, 3H), 2.16 (s, 3H), and 1.22 ppm (t, 3H).

Anal. for. C$_{13}$H$_{17}$Cl N$_2$O$_3$S:
Calcd.: C, 49.29; H, 5.41; N, 8.84.
Found: C, 49.32; H, 5.34; N, 8.65.

EXAMPLE 2

Ethyl [[[[(4-Chloro-2-methylphenyl)amino]thioxomethyl]methylamino]oxy]acetate

A mixture of 4-chloro-2-methylphenyl-isothiocyanate (5.5 g), ethyl N-methyl aminooxy acetate (4.0 g), and ether (30 mL) was stirred at ambient temperature for thirty minutes. The solvent was evaporated. Fresh ether (100 mL) was added then evaporated. Hexane (30 mL) was added then evaporated under vacuum. The residual oil solidified upon standing. The solid mass was slurried in hexane. The solid was collected by filtration and dried to give the title compound (9.3 g) as a white solid, m.p. 104–106° C. Mass spectrum (EI, M.$^+$) m/z 316/318. $^1$H-NMR (DMSO-$d_6$; 400 MHz) δ9.96 (s,1H), 7.34 (s, 1H), 7.25 (d, 1H), 7.19 (d, 1H), 4.69 (s, 2H), 4.18 (q, 2H), 3.54 (s, 3H), 2.17 (s, 3H), and 1.22 ppm (t, 3H).

Anal. for $C_{13}H_{17}ClN_2O_3S$:

Calcd.: C, 49.29; H, 5.41; N, 8.84.

Found: C, 49.54; H, 5.32; N, 8.86.

EXAMPLE 3

Ethyl [[[[(2,3-dihydro-1H-inden-5-yl)amino]thioxomethyl]methylamino]oxy]acetate

A mixture of 5-indanyl-isothiocyanate (8.75 g), ethyl N-methyl aminooxy acetate (6.65 g), and ether (100 mL) was stirred at ambient temperature for one hour. The solvent was evaporated. The residue was dissolved in fresh ether (200 mL) and washed with 2N hydrochloric acid (50 mL) then with water (50 mL). The organic phase was dried over anhydrous magnesium sulfate. Evaporation of the solvent afforded an oil that solidified upon standing. The solid was slurried in ether, collected by filtration and dried to give the title compound (9.1 g) as a white solid, m.p. 69–71° C. Mass spectrum (EI, M.$^+$) m/z 308. $^1$H-NMR (DMSO-$d_6$; 400 MHz) δ10.21 (s, 1H), 7.34 (s, 1H), 7.18 (s, 2H), 4.71 (s, 2H), 4.19 (q, 2H), 3.52 (s, 3H), 2.83 (q, 4H), 2.03 (m, 2H), and 1.22 ppm (t, 3H).

Anal. for. $C_{15}H_{20}N_2O_3S$:

Calcd.: C, 58.42; H, 6.54; N, 9.08.

Found: C, 58.20; H, 6.56; N, 9.10.

EXAMPLE 4

Ethyl [[methyl[[(2-(1-methylethyl)phenyl]amino]thioxomethyl]methylamino]oxy]acetate A mixture of 2-isopropylphenyl-isothiocyanate (8.85 g), ethyl N-methyl aminooxy acetate (6.65 g), and ether (100 mL) was stirred at ambient temperature for one hour. The solvent was evaporated. The residue was dissolved in fresh ether (200 mL) and washed with 2N hydrochloric acid (50 mL) then with water (50 mL). The organic phase was dried over anhydrous magnesium sulfate. Evaporation of the solvent afforded an oil that solidified upon standing. The solid was slurried in ether (30 mL) and hexane (70 mL). The solid was collected by filtration and dried to give the title compound (8.6 g) as a white solid, m.p. 57–58° C. Mass spectrum (EI, M.$^+$) m/z 310. $^1$H-NMR (DMSO-$d_6$; 400 MHz) δ9.98 (s, 1H), 7.33 (d, 1H), 7.27 (t, 1H), 7.18 (t, 1H), 7.11 (d, 1H), 4.69 (s, 2H), 4.18 (q, 2H), 3.54 (s, 3H), 3.04 (m, 1H), 1.22 (t, 3H), and 1.14 ppm (d, 6H).

Anal. for $C_{15}H_{22}N_2O_3S$:

Calcd.: C, 58.04; H, 7.14; N, 9.02.

Found: C, 57.79; H, 7.15; N, 9.05.

EXAMPLE 5

Ethyl [[[[(2,5-dimethylphenyl)amino]thioxomethyl]methylamino]oxy]acetate

A mixture of 2,5-dimethylphenyl-isothiocyanate (8.15 g), ethyl N-methyl aminooxy acetate (6.65 g), and ether (100 mL) was stirred at ambient temperature for one hour. The solvent was evaporated. The residue was dissolved in fresh ether (200 mL) and washed with 2N hydrochloric acid (50 mL) then with water (50 mL). The organic phase was dried over anhydrous magnesium sulfate and the solvent was evaporated. The residual oil was crystallized from ether/hexane mixture. The solid was collected by filtration and dried to give the title compound (8.7 g) as a white solid, m.p. 53–540° C. Mass spectrum (EI, M.$^+$) m/z 296. $^1$H-NMR (DMSO-$d_6$; 400 MHz) δ9.94 (s, 1H), 7.12 (d, 1H), 7.00 (d, 2H), 7.18 (t, 1H), 4.68 (s, 2H), 4.18 (q, 2H), 3.54 (s, 3H), 2.25 (s, 3H), 2.12 (s, 3H), and 1.22 ppm (t, 3H).

Anal. for $C_{14}H_{20}N_2O_3S$:

Calcd.: C, 56.73; H, 6.80; N, 9.45.

Found: C, 56.69; H, 6.86; N, 9.46.

EXAMPLE 6

Ethyl [[[[(2-methylpropyl)amino]thioxomethyl]methylamino]oxy]acetate

A mixture of isobutyl-isothiocyanate (5.75 g), ethyl N-methyl aminooxy acetate (6.65 g), and ether (100 mL) was stirred at ambient temperature for one hour. The solvent was evaporated. The residue was dissolved in fresh ether (200 mL) and washed with 2N hydrochloric acid (50 mL) then with water (50 mL). The organic phase was dried over anhydrous magnesium sulfate and the solvent was evaporated. The residual oil was chromatographed on silicagel (ethyl acetate/hexane, 1:19). The title compound (9.6 g) was obtained as an oil. Mass spectrum (EI, M.$^+$) m/z 248. $^1$H-NMR (DMSO-$d_6$; 400 MHz) δ 9.69 (t, 1H), 4.58 (s, 2H), 4.17 (q, 2H), 3.42 (s, 3H), 3.29 (q, 2H), 1.96 (m, 1H), 1.21 (t, 3H),and 0.87 ppm (d, 6H).

Anal. for $C_{10}H_{20}N_2O_3S$:

Calcd.: C, 48.36; H, 8.12; N, 11.28.

Found: C, 48.52; H, 8.44; N, 11.31.

EXAMPLE 7

Ethyl [[[[(4-phenoxyphenyl)amino]thioxomethyl]methylamino]oxy]acetate

A mixture of 4-phenoxyphenyl-isothiocyanate (11.35 g), ethyl N-methyl aminooxy acetate (6.65 g), and ether (100 mL) was stirred at ambient temperature for one hour. The solvent was evaporated. The residue was dissolved in fresh ether (200 mL) and washed with 2N hydrochloric acid (50 mL) then with water (50 mL). The organic phase was dried over anhydrous magnesium sulfate and the solvent was evaporated. The residual oil was chromatographed on silicagel (ethyl acetate/hexane, 1:19). The title compound (14.2 g) was obtained as oil. Mass spectrum (EI, M.$^+$) m/z 360. $^1$H-NMR (DMSO-$d_6$; 400 MHz) δ10.26 (s, 1H), 7.50–7.47 (m, 2H), 7.40–7.35 (m, 2H), 7.13 (t, 1H), 7.02–6.98 (m, 4H), 4.72 (s, 2H), 4.19 (q, 2H), 3.55 (s, 3H), and 1.21 ppm (t, 3H).

Anal. for. $C_{18}H_{20}N_2O_4S$:

Calcd.: C, 59.98; H, 5.59; N, 7.77.

Found: C, 60.08; H, 5.67; N, 7.87.

EXAMPLE 8

Ethyl [[[[(4-Chloro-2-methylphenyl)amino]thioxomethyl]ethylamino]oxy]acetate

A mixture of 4-chloro-2-methylphenyl-isothiocyanate (3.76 g), ethyl N-ethyl aminooxy acetate (2.94 g), and ether (100 mL) was stirred at ambient temperature for one hour. The solvent was evaporated. The solvent was evaporated. The residue was dissolved in ethyl acetate (200 mL) and washed with 1N hydrochloric acid (2×100 mL) then with water (100 mL). The organic phase was dried over anhydrous magnesium sulfate and the solvent was evaporated. The residue was chromatographed on silica gel (ethyl acetate/hexane, 1:8.5). The title compound (9.3 g) was obtained as a white solid, m.p. 69–71° C. Mass spectrum (EI, M.$^+$) 330/332. $^1$H-NMR (DMSO-d$_6$; 400 MHz) δ9.96 (s, 1H), 7.34 (s, 1H), 7.25 (d, 1H), 7.18 (d, 1H), 4.67 (s, 2H), 4.17 (q, 2H), 4.12 (q, 2H), 2.16 (s,3H), 1.21 (t, 3H), and 1.17 ppm (t, 3H).

Anal. for $C_{14}H_{19}ClN_2O_3S$:

Calcd.: C, 50.83; H, 5.79; N, 8.47.

Found: C, 50.85; H, 5.79; N, 8.45.

EXAMPLE 9

Ethyl [[[[(5-Chloro-2-methylphenyl)amino]thioxomethyl](1-methylethyl)amino]oxy]acetate A mixture of 5-chloro-2-methylphenyl-isothiocyanate (12 g), ethyl N-isopropyl aminooxy acetate (10.5 g), triethylamine (10 mL), and ether (20 mL) was stirred at ambient temperature for two hour. The solvent was evaporated. The residue was dissolved in ethyl acetate (400 mL) and washed with 2N hydrochloric acid (2×300 mL) then with brine (300 mL). The organic phase was dried over anhydrous magnesium sulfate and the solvent was evaporated. The residue was chromatographed on silica gel (ethyl acetate/hexane, 1:9). Crystallization from ether/hexane afforded the title compound (7.7 g) as a white solid, m.p. 83–85° C. Mass spectrum (EI, M.$^+$) m/z 344/346. $^1$H-NMR (DMSO-d$_6$; 400 MHz) δ10.12 (s, 1H), 7.30–7.24 (m, 3H), 5.28 (m, 1H), 4.72 (s, 2H), 4.17 (q, 2H), 2.14 (s, 3H), and 1.21 ppm (t, 9H).

Anal. for. $C_{15}H_{21}Cl N_2O_3S$:

Calcd.: C, 52.24; H, 6.14; N, 8.12.

Found: C, 52.33; H, 6.11; N, 8.12.

The present invention may be embodied in other specific forms without departing from the spirit and essential attributes thereof and accordingly, reference should be made to the appended claims, rather than to the foregoing specification, as indicating the scope of the invention.

What is claimed is:

1. Antiatherosclerotic compounds of the formula:

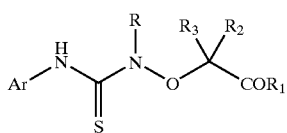

(I)

wherein

R is lower alkyl;

R$_1$ is hydroxy, amino, or lower alkoxy;

R$_2$ and R$_3$ are each independently hydrogen, alkyl or aryl;

Ar is phenyl, indanyl, benzhydryl, or phenyl substituted with one or more members selected from the group consisting of halogen, lower alkyl, perfluoroalkyl, lower alkoxy, perfluoroalkylalkoxy, dialkylamino, and aryloxy; or pharmaceutically acceptable salts thereof.

2. The antiatherosclerotic compounds of claim 1 wherein,

R is lower alkyl;

R$_1$ is lower alkoxy;

R$_2$ and R$_3$ are each hydrogen;

Ar is phenyl, indanyl, or phenyl optionally with one or more members selected from the group consisting of halogen, lower alkyl, lower alkoxy, and aryloxy; or pharmaceutically acceptable salts thereof.

3. The antiatherosclerotic compound of claim 1 which is Ethyl [[[[(5-Chloro-2-methylphenyl)amino]thioxomethyl]methylamino]oxy]acetate.

4. The antiatherosclerotic compound of claim 1 which is Ethyl [[[[(4-Chloro-2-methylphenyl)amino]thioxomethyl]methylamino]oxy]acetate.

5. The antiatherosclerotic compound of claim 1 which is Ethyl [[[[(2,3-dihydro-1H-inden-5-yl)amino]thioxomethyl]methylamino]oxy]acetate.

6. The antiatherosclerotic compound of claim 1 which is Ethyl [[methyl[[(2-(1-methylethyl)phenyl]amino]thioxomethyl]methylamino]oxy]acetate.

7. The antiatherosclerotic compound of claim 1 which is Ethyl [[[[(2,5-dimethylphenyl)amino]thioxomethyl]methylamino]oxy]acetate.

8. The antiatherosclerotic compound of claim 1 which is Ethyl [[[[(2-methylpropyl)amino]thioxomethyl]methylamino]oxy]acetate.

9. The antiatherosclerotic compound of claim 1 which is Ethyl [[[[(4-phenoxyphenyl)amino]thioxomethyl]methylamino]oxy]acetate.

10. The antiatherosclerotic compound of claim 1 which is Ethyl [[[[(4-Chloro-2-methylphenyl)amino]thioxomethyl]ethylamino]oxy]acetate.

11. The antiatherosclerotic compound of claim 1 which is Ethyl [[[[(5-Chloro-2-methylphenyl)amino]thioxomethyl](1-methylethyl)amino]oxy]acetate.

12. The antiatherosclerotic compound of claim 1 which is Ethyl [[[[(5-Chloro-2-methylphenyl)amino]thioxomethyl](1-methylpropyl)amino]oxy]acetate.

13. A pharmaceutical composition comprising an antiatherosclerotic compound of the formula:

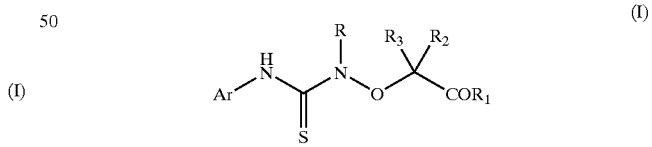

(I)

wherein

R is lower alkyl;

R$_1$ is hydroxy, amino, or lower alkoxy;

R$_2$ and R$_3$ are each independently hydrogen, alkyl or aryl;

Ar is phenyl, indanyl, benzhydryl, or phenyl substituted with one or more member selected from the group consisting of halogen, lower alkyl, perfluoroalkyl, lower alkoxy, perfluoroalkylalkoxy, dialkylamino, and aryloxy; or pharmaceutically acceptable salts thereof.

14. A method of treating atherosclerosis in a mammal in need thereof, which comprises administering to said mammal an anti-atherosclerotic effective amount of a compound of the formula:

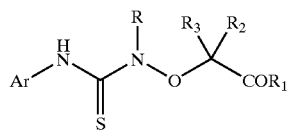

(I)

wherein

R is lower alkyl;

$R_1$ is hydroxy, amino, or lower alkoxy, $R_2$ and $R_3$ are each independently hydrogen, alkyl or aryl;

Ar is phenyl, indanyl, benzhydryl, or phenyl substituted with one or more member selected from the group consisting of halogen, lower alkyl, perfluoroalkyl, lower alkoxy, perfluoroalkylalkoxy, dialkylamino, and aryloxy; or pharmaceutically acceptable salts thereof.

* * * * *